Figure 2:
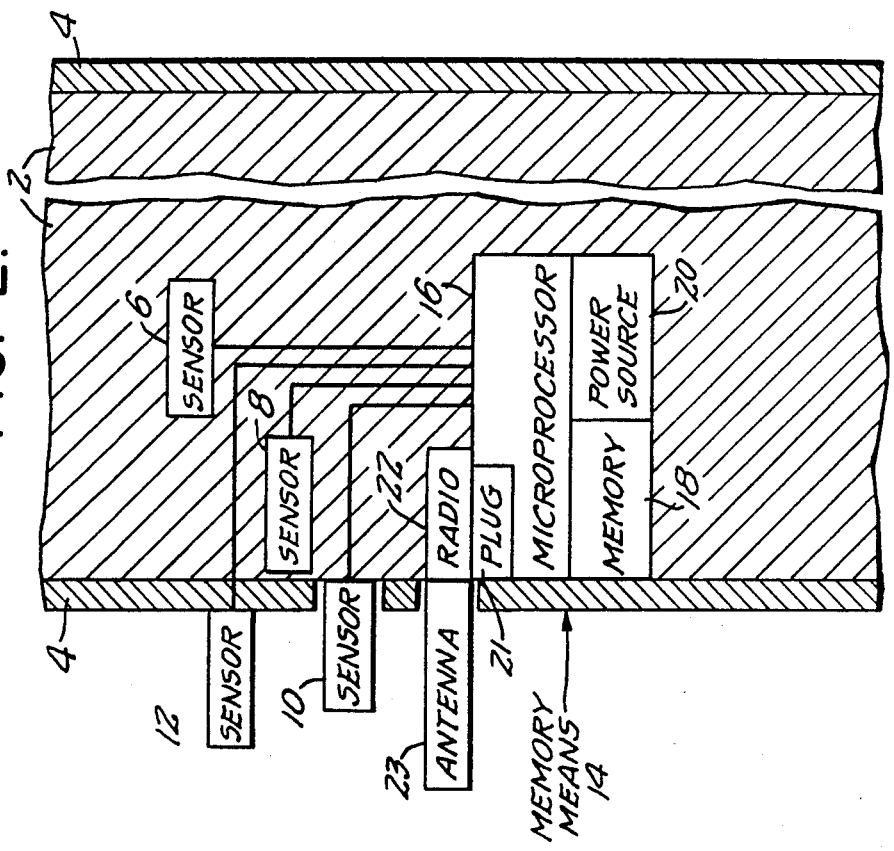

United States Patent [19]

Radjy

[11] Patent Number: 4,943,930
[45] Date of Patent: Jul. 24, 1990

[54] METHOD AND APPARATUS FOR NON-DESTRUCTIVE EVALUATION OF CONCRETE

[76] Inventor: Farrokh F. Radjy, Gateway Twrs. 18L, Pittsburgh, Pa. 15222

[21] Appl. No.: 434,564

[22] Filed: Nov. 8, 1989

Related U.S. Application Data

[63] Continuation of Ser. No. 853,682, Apr. 18, 1986, abandoned.

[51] Int. Cl.⁵ .............................................. G01N 3/26
[52] U.S. Cl. ..................................... 364/506; 364/552; 364/550; 374/45; 374/53; 73/803; 73/573
[58] Field of Search ................... 364/550, 551.01, 552, 364/506, 507, 508, 512, 468, 469, 476, 477; 73/78, 763, 767, 768, 801, 803, 573, 577, 634; 340/665, 980; 374/45, 53, 54, 102, 103

[56] References Cited

U.S. PATENT DOCUMENTS

| 4,398,427 | 8/1983 | Pan | 73/784 |
|---|---|---|---|
| 4,433,385 | 2/1984 | DeGasperi et al. | 364/507 |
| 4,515,545 | 5/1985 | Hinrichs et al. | 364/508 |
| 4,538,467 | 9/1985 | Stoll | 73/803 |
| 4,566,806 | 1/1986 | DeBondt | 374/45 |
| 4,603,395 | 7/1986 | Steinberger | 364/506 |
| 4,604,706 | 9/1986 | Fisher, Jr. et al. | 364/507 |
| 4,715,726 | 12/1987 | Tsuruta | 364/506 |

FOREIGN PATENT DOCUMENTS 736002 5/1980 U.S.S.R. ............................... 73/803

Primary Examiner—Parshotam S. Lall
Assistant Examiner—Brian M. Mattson
Attorney, Agent, or Firm—Lucas & Just

[57] ABSTRACT

The method and apparatus for the non-destructive evaluation of a concrete mass uses the maturity method for evaluating the strength and durability of the concrete mass. The apparatus employs sensors which are implanted in the concrete along with a microprocessor and non-volatile RAM or EEPROM. A microcomputer is used periodically to up load the RAM and to make an evaluation of the concrete mass.

17 Claims, 3 Drawing Sheets

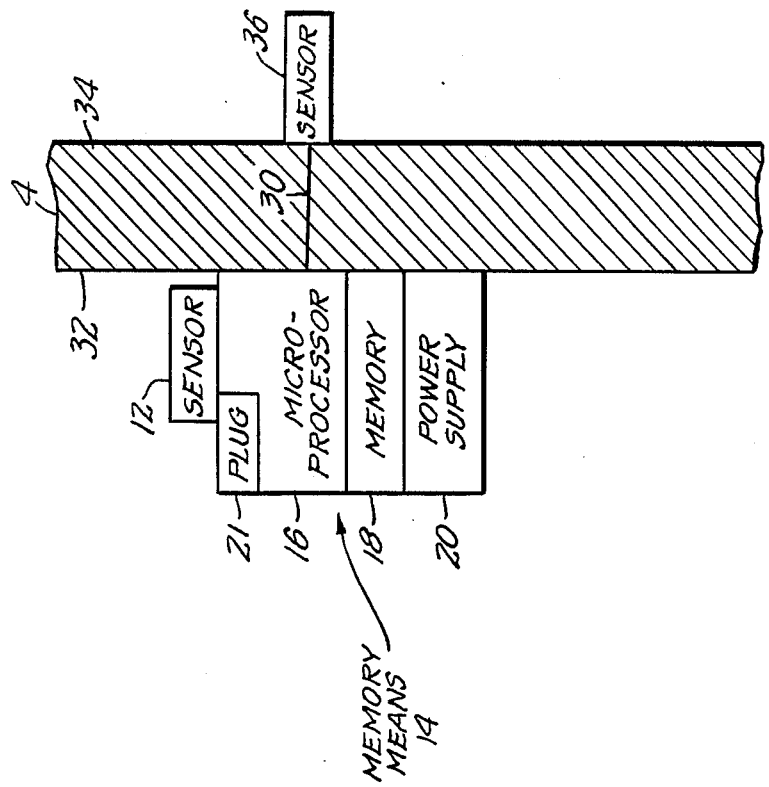

METHOD AND APPARATUS FOR NON-DESTRUCTIVE EVALUATION OF CONCRETE

This is a continuation of application Ser. No. 853,682, filed Apr. 18, 1986, now abandoned.

This invention relates to the construction field and, more particularly, to non-destructive testing and evaluation of concrete to determine the strength and durability thereof.

Concrete is generally used within the industry to refer to a mixture of cement, sand, stone, and water which upon aging turns into a hardened mass. The term concrete, as used in the specification and claims herein, means not only concrete as it is generally defined in the industry (cement, sand and stone), but it also means mortar (cement, sand and water) and cement (cement and water which hardens into a solid mass upon aging).

The term concrete mass which is used in the specification and claims means a mass or body which is made from concrete, mortar, cement, or the like. This is in contrast to the term concrete form which, when used in the specification and claims, means the structures into which concrete is poured that allows the concrete mass to hold its shape during hardening.

In the construction field, there is a need to predict the in-place strength of a concrete mass. A driving force is the economic benefit that can be derived by using accelerated construction schedules, but such acceleration requires means to monitor in-place strength so that structural safety can be maintained at all times.

There are available several methods for testing and monitoring in-place strength of a concrete mass which have been incorporated into the American Standard Testing Methods.

1. ASTM C805: The Rebound Number Method—the so-called Swiss Hammer Method.
2. ASTM C597: The Pulse Velocity (Sonic) Method.
3. ASTM C900: The Pullout Strength Method.

It has been found that the strength of a given concrete mass is a function of the time and the temperature history of the mass. This method has come to be known as the maturity method and one version of it is founded in the Arrhenius equation that the rate of a chemical reaction is an exponential function of the temperature. A current discussion of the maturity method is contained in an article by N. J. Carino, in Vol. 6 No. 2 of ASTM Journal of Cement, Concrete and Aggregates, Winter 1984. The maturity method is used to predict the in-place strength of a concrete mass based on its thermal history. By monitoring the temperature and recording the time and temperature history of the concrete mass, the strength of the concrete mass is determined. A suitable formula proposed by P. Freiesleben Hansen and Erik J. Pedersen of Beton-Og-Konstruktionsinstituttet of Denmark, for making such a calculation is Formula (1) below.

A comparison of the speed at 20° C. with the speed at $\theta$° C. will give the following approximate proportion:

$$H(\theta) = \frac{\text{speed at } \theta° C.}{\text{speed at } 20° C.} = \exp\left[\frac{E}{R} \cdot \left(\frac{1}{293} - \frac{1}{273 + \theta}\right)\right] \quad (1)$$

where $E$ = characteristic activation energy
$\quad$ = 33500 J/mole for $\theta \geq 20°$ C. $\quad$) for
$\quad\quad$ 33500 + 1470 · (20 − $\theta$) J/mole $\quad$} portland
$\quad\quad$ for $\theta < 20°$ C. $\quad\quad\quad\quad\quad\quad$) cement $R$ = the gas constant, 8.314 J/mole °C.

Through application of the temperature function $H(\theta)$, it is possible to compare hardening processes at a temperature $\theta$ with an already known hardening process examined at the reference temperature of 20° C. This comparison is made by calculating the maturity M of the concrete which is the equivalent age at 20° C. The maturity of the concrete is determined by:

$$M = \int_0^t H(\theta) \cdot d\tau \quad (2)$$

The heat development as a function of the maturity M to a good approximation is represented by:

$$Q(M) = Q_\infty \cdot \exp\left[-\left(\frac{\tau_e}{M}\right)^\alpha\right] \quad (3)$$

where
$Q_\infty$ = total heat development for M $\infty$, kJ/kg
$Q(M)$ = heat development at maturity M, kJ/kg
M = the maturity of the concrete, hours, from Eq. (2)
$\tau_e$ = characteristic time constant, hours
$\alpha$ = curve parameter, dimensionless The strength development can, with a good approximation, be described through the parameters $\sigma_\infty$, $\tau_e$ and $\alpha$ through the equation:

$$\sigma(M) \simeq \sigma_\infty \cdot \exp\left[-\left(\frac{\tau_e}{M}\right)^\alpha\right] \quad (4)$$

where:
$\sigma_\infty$ = potential final strength, MPa, for M→∞
$\sigma(M)$ = strength at the maturity M, MPa
M = maturity of the concrete, hour, from Eq. (2)
$\tau_e$ = characteristic time constant, hours
$\alpha$ = curve parameter, dimensionless Equation (4) is purely empirical. Usually, the quantities $\tau_e$ and $\alpha$ will vary from the corresponding values for heat development in (3).

As is apparent from these calculations above, maturity of the concrete mass is calibrated using a controlled sample at 20° C.

An efficient and economical apparatus and method for monitoring the curing temperature and time and for determining the strength of the concrete mass has now been discovered.

Broadly, temperature sensors are attached to a concrete mass after it has been poured. The sensors are connected to a memory means. The memory means is capable of recording temperature data from the sensor at different times to establish the time and temperature history of the mass. The memory means is preprogrammed with an instruction on which sensor to read and the frequency of those readings. After the concrete mass has hardened, or during the hardening process, the memory means is tapped or up loaded into a computer. The computer then utilizes the maturity method to calculate the strength of the concrete mass from the time and temperature history of the mass. As is apparent from the above discussion of the maturity method, each batch of concrete requires a sample of concrete as poured to 'calibrate' the maturity equations. This calibration sample is used to 'calibrate' or 'zero' the maturity method equation for use in the computer. If each sample is of the same make-up, the device does not need to be re-zeroed but only periodically checked for accuracy. However, each different make-up of concrete should be tested in order to calibrate the device and provide accurate predictions of the strength.

One of the great advantages of the present invention is that the memory means is attached to the concrete mass allowing data to be collected inexpensively since the equipment used to make up the memory means is conventional and inexpensive.

Another great advantage of the present invention is that at the convenience of the user, the computer is connected to the memory means, and the information from the memory means is up loaded into the computer. Thus, a construction project can attach sensors and memory means to concrete masses, and at some later date, a worker goes to the hardened or hardening concrete mass and connects a computer to the memory and up loads the data into the computer. Thus, a construction operation needs only one computer for calculating the strength of the multiple concrete structures and at multiple sites.

Furthermore, since the memory means are capable of autonomous operation, the central or the site computer need not be engaged in the maturity monitoring task on a continuous basis and can even be totally turned off during nights or when the site is shut down.

Additionally, the memory means may be attached to precast components, which are typically cast at a pre-casting plant and then shipped to the construction site, for continous monitoring and recording of temperature development during transport or curing in order to evaluate the sufficiency of strength for loading or post-tensioning. After arrival at the construction site, the memory means is tapped by the maturity computer system for interpreting the accumulated data.

Another advantage of the memory means system is that the readings recorded from multiple sensors can be transmitted serially through a single channel instead of having to deal with a multitude of sensors at any given instant of time. This simplifies the problem of communications on a construction site making the maturity method a practical tool.

Additionally, little expertise is needed to connect the computer to the memory means and interpret the collected data, whereas in the ASTM methods referred to above, a great deal of technical expertise is needed to perform the respective tests and their interpretation.

Another advantage of the present invention is that sonic sensors or probes may also be used in the system of the present invention to generate data in a known manner for monitoring the long term durability of the hardened concrete mass.

Suitable temperature sensors for use in accordance with the present invention are thermocouples, thermistors or RTD. Suitable sonic sensors for use in accordance with the present invention are sold by James Instruments Inc. as their V-meter or F-meter series. Both temperataure sensors and sonic sensors are conventional pieces of equipment readily available in the market. Suitable temperature sensors are sold under the brand names of Abbeon Cal. Inc. or Leeds and Northrup. The temperature sensors provide data for the strength determination, while the sonic probe provides data for monitoring the long term durability of the hardened concrete mass and both sets of data are fed to the memory means for use in the computer.

The sensors are attached to the concrete mass in a number of ways. One method is to implant sensors into the concrete mass as it is being poured or just after pouring. These implanted sensors are spaced at different points along the length of the concrete mass and at different depths in the concrete mass. These sensors are connected by wires to the outside of the mass. Another point of attachment is on the outside of the concrete mass itself along the surface of the concrete mass. A third point of attachment is affixing the sensors onto the outside of the concrete form in which the mass is hardening. This third point provides reference data.

Preferably, multiple sensors are placed at various locations inside the mass and along the surface of the mass, while only one sensor is placed on the outside of the form as a reference.

The sensors are left in the concrete after it has hardened or, alternatively, they are removed after hardening. It is also possible to place sensors only in the forms which hold the concrete while it is hardening, and thus, once the form is removed from around the hardened concrete so too are the sensors removed. The sensors attached to the form can be implanted in the concrete and removed when the form is removed.

Placement of both the temperature and sonic sensors are such that they do not interfere with each other.

The memory means is made up of a microprocessor and a memory. The sensors are connected, typically by a wire, to the microprocessor which in turn is connected, typically by a wire, to the memory. A power source is included in the memory, microprocessor or both or is a separate unit attached to the memory or microprocessor or both. The microprocessor converts the signals from the sensors into the data required for storage in the memory and for use in the computer. The microprocessor is preprogrammed to accept the signals from the sensors at preprogrammed times and to convert those signals into data for storage in the memory. The microprocessor is preprogrammed to convert the signals obtained from the sensors into data which is not only able to be stored in the memory, but also into data which is acceptable to the computer. The microprocessor is preprogrammed to accept signals from temperature sensors, sonic sensors or both and to convert those signals into data which is stored in the memory and is acceptable to the computer. Preferably, the microprocessor is able to be reprogrammed after it has been installed in the concrete mass. This preprogramming is preferably accomplished with the same computer used to calculate strength of the concrete mass.

Microprocessors are conventional pieces of equipment well-known to those of skill in the art, and the microprocessor is programmed in conventional manner to convert signals received from the sensors into the data desired for storage in the memory and acceptable by the computer. Suitable microprocessors for use in this invention are sold under the brand names of Intel, Motorola and National. Preferably, only one microprocessor is used per concrete slab or form.

Suitable memory includes non-volatile RAM or EEPROM. In fact, non-volatile RAMs or EEPROMs are preferred. Non-volatile RAMs are conventional pieces of equipment and are readily available in the market and sold under the trade name Xicor. EEPROM are conventional pieces of equipment and are readily available in the market sold under the brand names Advance Micro Device, Xicor, Intel and SEEQ Technology.

The memory means is attached to the concrete mass by affixing the memory means to the outside of the concrete mass or to the outside of the concrete form in which the mass is hardening. Alternatively, the memory means is attached to the concrete mass by implanting whole or part of the memory means into the concrete mass. For example, the memory, microprocessor and a power source are implanted inside the concrete, and wires lead out of the concrete to a suitable position for tapping. In another example, the memory and microprocessor are implanted into the concrete while the power source is outside the concrete. This allows replacement of the power source. Wires connect from the implanted memory means to the outside for tapping.

The next step in the process is to tap the memory means. Tapping is accomplished by connecting the memory means to a computer and then up loading the memory means into the computer. Conventional circuitry is used to interface between the computer and the memory means.

Preferably a so-called personal computer or microcomputer is used for the computer. These are conventional pieces of equipment readily available. Suitable microcomputers are sold under the trade names IBM PC, IBM XT and COMPAQ Portable or Professional.

An interface modem is used between the memory means and the computer to allow the memory means to up load into the computer. Such a piece of equipment is conventional and often part of the microcomputer. The operation of such is well-known to those of skill in the art.

The computer is programmed to use a maturity method for calculating the strength of the concrete in a conventional manner. Programs for using the maturity method are conventional and readily available in the marketplace. One suitable program is sold by Beton-Og Konstruktionsinstituttet, Dr. Neergaards Vej 13, Postboks 82, DK-2970 Horsholm, Denmark. In fact, very good results have been found with this program. The computer is also programmed in a conventional manner with a conventional program for evaluating the sonic data obtained from the memory means and to determine the long term durability of the hardened concrete mass. Another advantage to the present invention is that sophisticated environmental data, such as weather conditions like wind speed, can be inputted into the computer to allow for more precise calculations of the strength of the concrete mass.

The tapping step is accomplished by connecting the computer to the memory means by a wire. Alternatively, the connection is an electromagnetic signal, such as a radio or optical signal. The connection between the computer and the memory means is dictated by expense and ease of hookup. It is hard for a concrete structure under the sea to be connected to a computer on land by wire; rather, it is much simpler to use a radio-type transmitter-receiver incorporated in known manner into the memory means for feeding data to the computer using conventional radio-type signals between the memory means and the computer.

These and other aspects of the present invention are highlighted by reference to the drawings wherein:

FIGS. 1-5 illustrate some preferred placement of the apparatus of the present invention in the concrete mass to be monitored.

Figure 1:
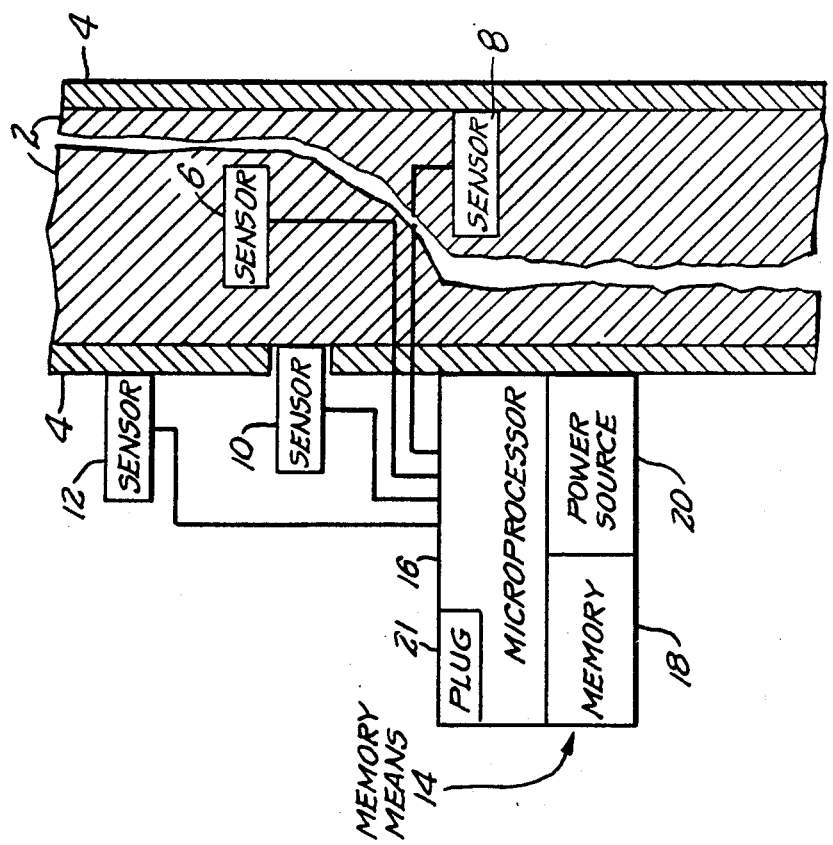

FIG. 1 illustrates concrete 2 surrounded by concrete form 4. Sensor 6 is implanted in the center of concrete mass 2, sensor 8 is implanted near the surface of concrete mass 2, and sensor 10 is on the surface of concrete mass 2. Sensor 12 is a reference sensor which is placed on the outside of concrete form 4. Memory means 14 is placed on the outside of concrete form 4 and is removed along with the sensors when form 4 is removed. Memory means 14 is made up of microprocessor 16, memory 18 and power source 20. The memory means is connected to the sensors as shown. Tapping plug 21 is shown where the computer is connected to memory means 14 for up loading into the computer.

FIG. 2 has all the components of FIG. 1 except that memory means 14 is implanted in the surface of concrete mass 2, and radio transmitter 22 with antenna 23 is connected to memory means 14. Such a configuration is used under water or on land to reach placements of the memory means.

Figure 3:
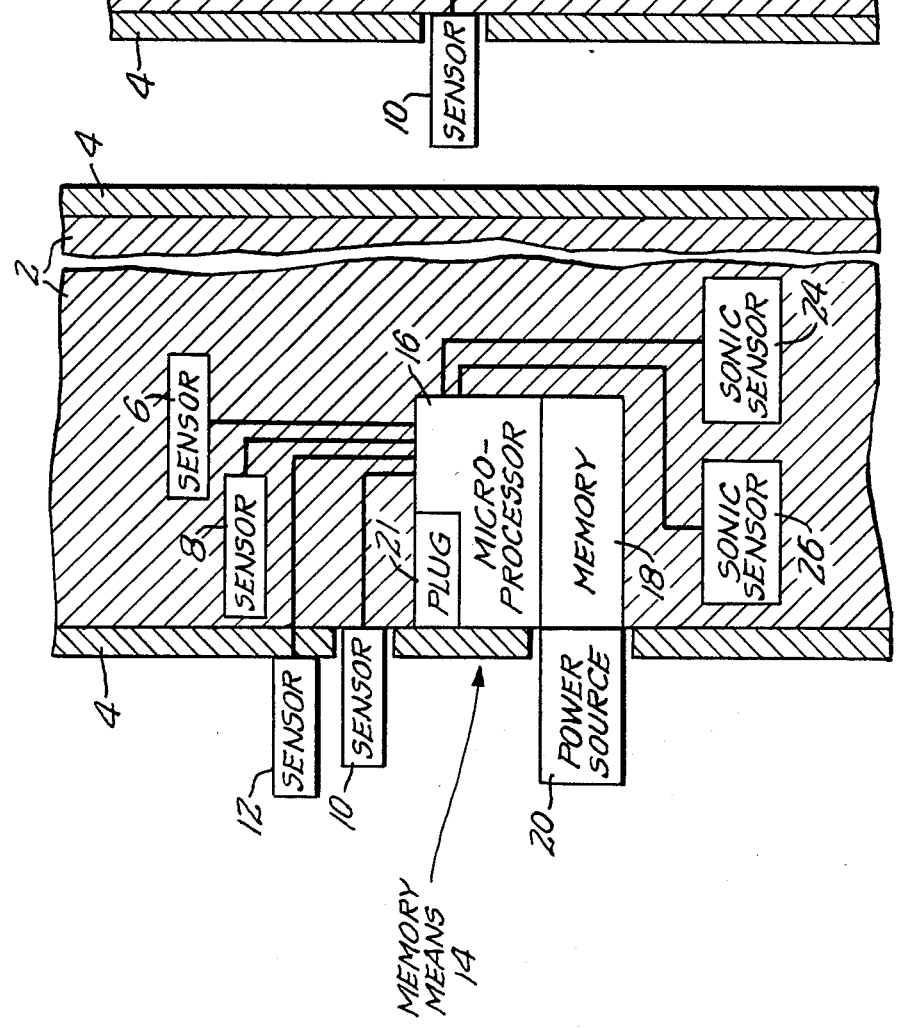

FIG. 3 shows all of the character references 2-14 identified in FIG. 1 and sonic sensors 24 and 26. These are conventional sonic sensors. Power source 20 is mounted on the outside of concrete mass 2 while microprocessor 16 and memory 18 are implanted therein.

Figure 4:
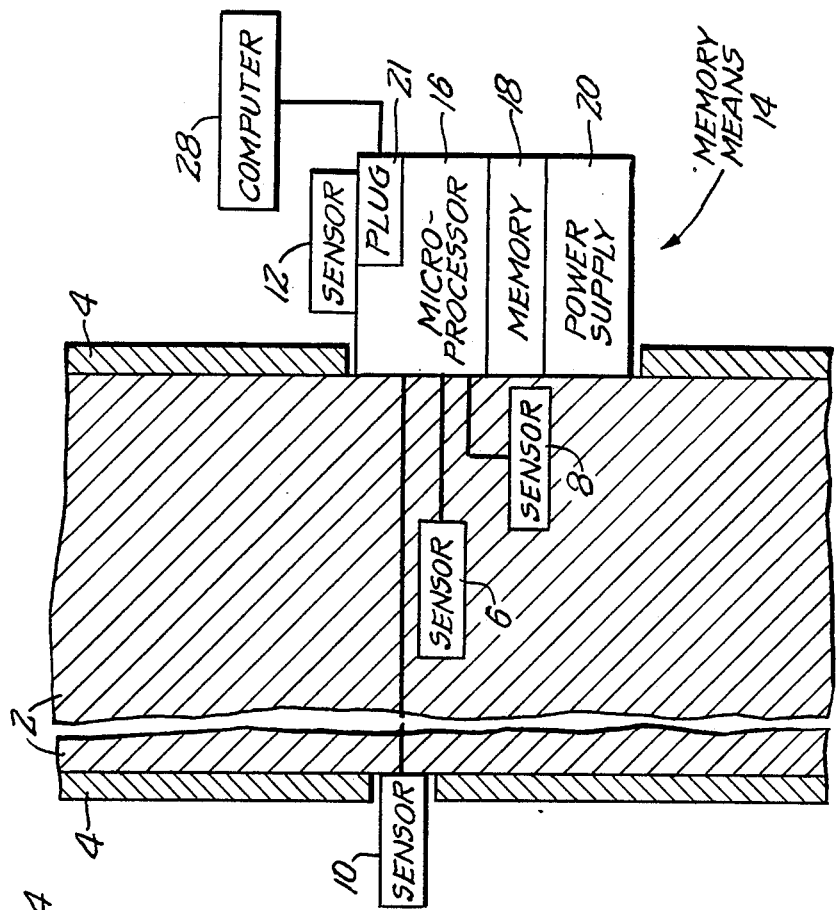

FIG. 4 illustrates memory means 14 placed on the outside of concrete mass 2. When forms 4 are removed, memory means 14 is left behind. Reference sensor 12 is on the outside of memory means 14. Computer 28 is shown connected to plug 21 for up loading memory means 14.

In more sophisticated construction, concrete forms are made in a separate operation from the construction site. Such forms are often molded or formed from plastic-like materials, such as thermoplastic resins, or made from steel and wood. In such a form, the memory means is mounted or built into the form by the manufacturer and then sold to the contractor for use at the job site or for precasting of the concrete mass. FIG. 5 illustrates one embodiment of a premade concrete form with a memory means attached thereto. FIG. 5 illustrates a premade concrete form 4 with a memory means 14 attached. Memory means 14 has reference sensor 12, microprocessor 16, memory 18, power source 20 and tapping plug 21. Wires 30 connect the memory means which is mounted on outside wall 32 of form 4 to the inside wall 34 of form 4. On inside wall 34 of form 4, wires 30 connect to plug 36. Obviously, sensors could be placed or built into the form and already connected to the memory means when sold to the user.

All of the drawings, FIGS. 1-5, illustrate the use of a wire to connect the sensors to the memory means.

It will be understood that it is intended to cover all changes and modifications of the preferred embodiment of the present invention herein chosen for the purpose of illustration which do not constitute a departure from the spirit and scope of the invention.

What is claimed is:

1. A method for non-destructive strength evaluation of a concrete mass comprising:
   (a) implanting an internal temperature sensor in said concrete mass before said concrete mass has hardened;
   (b) attaching a reference temperature sensor externally to said concrete mass before said concrete mass has hardened;

(c) attaching a microprocessor to said internal temperature sensor and to said reference temperature sensor such that signals from said internal temperature sensor and said reference temperature sensor are transmitted to said microprocessor and recorded by said microprocessor, thereby obtaining a temperature profile of said concrete mass; and (d) tapping said microprocessor with a computer thereby down loading said microprocessor into said computer whereby said computer evaluates the strength of said concrete mass.

2. The method of claim 1 wherein said microprocessor is connected to a memory device selected from the group consisting of a non-volatile RAM and a EEPROM.

3. The method of claim 2 wherein the internal and the reference temperature sensors are selected from the group consisting of a thermocouple, and a resistor thermometric device.

4. The method of claim 1 wherein the tapping of said microprocessor is accomplished by a wire connected between the computer and the microprocessor.

5. The method of claim 1 wherein the tapping of said microprocessor is accomplished by means of a radio transmitter-receiver connected to said microprocessor.

6. The method of claim 1 further comprising the step of implanting a sonic sensor in said concrete mass before said concrete mass has hardened and connecting said sonic sensor to said microprocessor.

7. The method of claim 1 wherein said reference temperature sensor, said internal temperature sensor and said microprocessor are affixed directly to a premade concrete form used to mold said concrete mass such that said microprocessor, said reference temperature sensor and internal temperature sensor are removed from said concrete when said premade concrete form is removed from said concrete mass.

8. The method of claim 1 wherein said internal temperature sensor, said reference temperature sensor and said microprocessor are affixed directly to said concrete mass.

9. A method for non-destructive strength evaluation of a concrete mass comprising:

(a) implanting a temperature sensor in said concrete mass before said concrete mass has hardened;

(b) attaching a reference temperature sensor to said concrete mass;

(c) affixing a microprocessor to said concrete mass and connecting said microprocessor to said implanted sensor and said reference sensor, said microprocessor being programmed to periodically record signals from said implanted sensor and said reference sensor;

(d) affixing a memory to said concrete mass and connecting said memory to said microprocessor to record data obtained by said microprocessor from said implanted sensor and said reference sensor; and (e) tapping said microprocessor with a computer, thereby up loading said microprocessor into said computer whereby said computer evaluates the strength of said concrete mass.

10. An apparatus for non-destructive strength evaluation of a concrete mass comprising:

(a) an internal temperature sensor for implanting in said concrete mass;

(b) a reference temperature sensor for attaching externally to said concrete mass;

(c) a microprocessor connected to said internal temperature sensor and said reference temperature sensor, said microprocessor for recording signals from said internal temperature sensor and said reference temperature sensor;

(d) a computer for evaluating signals from said microprocessor; and (e) means for transferring from said microprocessor said signals from said internal temperature sensor and said reference temperature sensor to said computer such that said computer can determine the strength of said concrete mass.

11. The apparatus of claim 10 wherein said means for transferring is a radio transmitter-receiver connected to said microprocessor.

12. The apparatus of claim 10 wherein the means for transferring is wire connecting said microprocessor to said computer.

13. The apparatus of claim 10 wherein said internal temperature sensor and said reference temperature sensor are selected from the group consisting of a thermocouple, and a resistor thermometric device.

14. An apparatus for non-destructive strength evaluation of a concrete mass comprising:

(a) a temperature sensor for implanting in said concrete mass before said concrete mass has hardened;

(b) a reference temperature sensor for attaching externally to said concrete mass;

(c) a microprocessor for receiving signals from said sensors;

(d) a memory for storing said signals obtained from said sensors; and (e) a computer for tapping and evaluating the signals stored in said memory thereby evaluating the strength of said concrete mass.

15. The apparatus of claim 14 further comprising a sonic sensor for implanting in said concrete mass prior to said concrete mass hardening, said sonic sensor connected to microprocessor.

16. A premade concrete form for non-destructive strength evaluation of a concrete mass comprising:

(a) a premade concrete form for casting concrete;

(b) a microprocessor attached to said premade concrete form;

(c) an internal temperature sensor connected to said microprocessor for insertion into said concrete mass;

(d) a reference temperature sensor connected to said microprocessor; and (e) means for transferring signals stored in said microprocessor from both said internal temperature sensor and said reference temperature sensor to a computer such that the strength of said concrete mass can be evaluated.

17. The premade concrete form of claim 16 wherein the means for transferring is a radio transmitterreceiver connected to said premade concrete form and said microprocessor.

* * * * *